(12) United States Patent
Gomez et al.

(10) Patent No.: US 11,642,449 B2
(45) Date of Patent: May 9, 2023

(54) SPECIALIZED SUCTION IRRIGATOR WITH CLOT BUSTING AND ANTI-CLOGGING FEATURES

(71) Applicant: New Wave Endo-Surgery Inc., Coconut Creek, FL (US)

(72) Inventors: Ricardo Alexander Gomez, Lighthouse, FL (US); Eric Allen Lopez, North Lauderdale, FL (US); Theo Dienes, Boca Raton, FL (US)

(73) Assignee: NEW WAVE ENDO-SURGICAL CORP., Coconut Creek, FL (US)

( * ) Notice: Subject to any disclaimer, the term of this patent is extended or adjusted under 35 U.S.C. 154(b) by 487 days.

(21) Appl. No.: 16/654,506

(22) Filed: Oct. 16, 2019

(65) Prior Publication Data

US 2020/0129676 A1    Apr. 30, 2020

Related U.S. Application Data

(60) Provisional application No. 62/749,721, filed on Oct. 24, 2018.

(51) Int. Cl.
*A61M 1/00* (2006.01)
*A61B 17/34* (2006.01)

(52) U.S. Cl.
CPC .......... *A61M 1/79* (2021.05); *A61B 17/3423* (2013.01); *A61M 1/84* (2021.05);
(Continued)

(58) Field of Classification Search
CPC ........ A61B 17/3423; A61B 2017/3443; A61B 2217/005; A61B 2217/007;
(Continued)

(56) References Cited

U.S. PATENT DOCUMENTS 3,669,116 A * 6/1972 Heyer ................. A61M 25/007
604/268
3,777,743 A * 12/1973 Binard ............... A61B 10/0291
606/119

(Continued)

FOREIGN PATENT DOCUMENTS

DE    202005009718    11/2006

OTHER PUBLICATIONS

International Search Report issued in corresponding PCT Application No. PCT/US2019/056525 dated Feb. 4, 2020.

*Primary Examiner* — Adam Marcetich
(74) *Attorney, Agent, or Firm* — Grogan, Tuccillo & Vanderleeden, LLP

(57) ABSTRACT

A laparoscopic anti-clogging device suitable for abdominal surgeries whose main function is to overcome the deficiencies caused by the clogging of a suction tool used in suction irrigation. More specifically an improved suction unclogging means used in Laparoscopic Suction Irrigator Systems (LSIS) that is used in the removal of bodily fluids, exudate and or bodily materials from the abdomen of a patient, allowing suction of a high-volume fluid in deep cavities and prevents interrupting fluid flow due to tissues clogging the device, and having the ability of being modified intra-abdominally to then focus all of its vacuum force on the distal opening, thereby facilitating blood clot busting and suction of solidified fluids as well as directed irrigation.

16 Claims, 12 Drawing Sheets

(52) U.S. Cl.
CPC . *A61B 2017/3443* (2013.01); *A61B 2217/005* (2013.01); *A61B 2217/007* (2013.01)

(58) Field of Classification Search
CPC ........ A61B 2010/0208; A61B 10/0283; A61B 2010/045; A61B 2017/32007; A61M 1/79; A61M 1/84; A61M 2205/0216; A61M 2205/7545; A61M 2206/20; A61M 2210/1021; A61M 1/76; A61M 1/77; A61M 1/774; A61M 1/87; A61M 25/007
See application file for complete search history.

(56) References Cited

U.S. PATENT DOCUMENTS

| | | | | |
|---|---|---|---|---|
| 4,400,168 A * | 8/1983 | Buechel | ............... | A61M 1/741 604/93.01 |
| 4,420,985 A * | 12/1983 | Raskin | ................. | G01L 1/2225 73/862.633 |
| 4,655,743 A | 4/1987 | Hyde | | |
| 5,041,093 A * | 8/1991 | Chu | .................... | A61B 17/221 606/198 |
| 5,833,632 A * | 11/1998 | Jacobsen | ............... | A61M 25/09 606/41 |
| 5,902,264 A | 5/1999 | Toso et al. | | |
| 6,024,730 A * | 2/2000 | Pagan | ............... | A61M 16/0465 604/525 |
| 6,066,149 A * | 5/2000 | Samson | ............... | A61B 17/221 606/127 |
| 2005/0033265 A1* | 2/2005 | Engel | ............... | A61M 25/0023 604/523 |
| 2005/0043682 A1* | 2/2005 | Kucklick | ........... | A61B 17/3421 604/167.03 |
| 2005/0096691 A1* | 5/2005 | Groothuis | ........ | A61B 17/12136 606/200 |
| 2005/0107736 A1* | 5/2005 | Landman | ............. | A61M 31/00 604/93.01 |
| 2005/0279359 A1* | 12/2005 | LeBlanc | ........... | A61M 25/0111 128/207.14 |
| 2006/0189896 A1* | 8/2006 | Davis | ................... | A61M 25/09 600/585 |
| 2007/0129682 A1* | 6/2007 | Eidenschink | ......... | A61M 25/09 604/164.13 |
| 2007/0173764 A1* | 7/2007 | Greeson | ................. | A61M 1/84 604/171 |
| 2008/0200946 A1* | 8/2008 | Braun | ................... | A61M 25/01 606/198 |
| 2010/0056862 A1* | 3/2010 | Bakos | ............... | A61B 17/3478 600/106 |
| 2013/0338580 A1* | 12/2013 | Yamatani | ................ | A61M 1/84 604/525 |
| 2014/0018732 A1* | 1/2014 | Bagaoisan | ........ | A61M 25/0136 604/95.04 |
| 2014/0276051 A1* | 9/2014 | Hoffman | ............ | A61B 17/3417 604/164.09 |
| 2015/0005792 A1* | 1/2015 | Ahn | ..................... | A61B 17/221 606/159 |
| 2016/0220269 A1 | 8/2016 | Labropoulos et al. | | |
| 2017/0056571 A1 | 3/2017 | Santanello | | |
| 2018/0126122 A1* | 5/2018 | Cabiri | .................. | A61B 1/0057 |
| 2018/0280671 A1* | 10/2018 | Parr | ................... | A61B 17/1204 |
| 2020/0069852 A1* | 3/2020 | Pastron | ................ | A61M 25/01 |

\* cited by examiner

SPECIALIZED SUCTION IRRIGATOR WITH CLOT BUSTING AND ANTI-CLOGGING FEATURES

CROSS-REFERENCE TO RELATED APPLICATIONS

This application claims the priority benefit of U.S. Provisional Patent Application Ser. No. 62/749,721 filed on Oct. 24, 2018, titled "Specialized Suction Irrigator with Clot Busting and Anti-Clogging Features" having the same inventors, and is hereby incorporated by reference for all that is disclosed as though fully set forth herein.

FIELD OF INVENTION

The present invention relates to the field of laparoscopic surgery specifically, suction irrigator systems used in laparoscopic surgery for clot busting.

BACKGROUND OF INVENTION

The background of the present invention relates to Endoscopic Suction Irrigation Systems (ESIS), used in laparoscopic surgery. These devices are used to remove fluids inside the body. They irrigate and evacuate clots. In the field of laparoscopic surgery, suction irrigators are used to remove fluids, exudate, and small bodily tissues from an area usually in the abdominal cavity. During surgery its normal for fluids and bodily tissues to accumulate in the body cavity. To remove the excessive fluids a suction device is used, typically having a cannula type configuration with an opening at its distal end. For most applications this configuration works well, except when the main orifices become clogged from soft tissues. The clogging action requires the surgeon to stop the surgery and attend to clearing up the blockage. These delays prolong the surgery and increase the risk for infections and complications.

One of the primary functions of a suction irrigator device is to continually evacuate fluids. Clogging is a problem that often occurs. Typically, to overcome the clogging problems associated with suction irrigators, and in order to maximize fluid evacuation, multiple symmetrically-located holes or openings are incorporated along the distal end of the cannula. Even though this helps with clogging issues, it does make the suction function less effective. In particular, the openings allow the suction device to continue operating when one of the holes becomes clogged, but the openings also reduce the suction at the distal end, thereby making the device less effective at evacuating blood clots.

It should be noted that there continues to be a need in the field for a suction irrigator device that minimizes clogging and maximizes suction power at the distal end. Therefore, in a continuing effort to improve on surgical suction irrigation systems, the present invention has been developed to overcome these and other similar deficiencies.

Additional attempts at addressing these issues have heretofore focused on adding extra holes along the shaft of the device to improve the suction force. However, since there is no skirt or blocking mechanisms along that shaft to restrict the additional airflow created by the additional holes, the additional holes become counterproductive for several reasons. First the device is used as an irrigator and the additional holes disperse the fluid and create erratic irrigation. The exposed holes suck more air than fluids, and actually weaken the sucking force of the device at the distal end. By adding new holes near the proximal end, the effective suction action of the device diminishes. Moreover, when the distal holes become clogged, instead of sucking harder and clearing the clot, the extra holes cause more air to be syphoned at the proximal end which, in turn, lessens sucking force at the distal end. The additional sucking force created by the additional holes is only effective when there are large amounts of fluids in the body cavity. Additionally, intraabdominal clots and tissues can clog the suction holes, preventing any suction from occurring.

The inventors of the present application have not found a similar device and believe this invention to be novel. In view of the above, there is a need in the field for a laparoscopic suction device that maintains its suction force throughout its use especially when clogging occurs.

SUMMARY OF INVENTION

The present invention relates to an improved suction anti-clogging means used in Laparoscopic Suction Irrigator Systems (LSIS), primarily for the removal of bodily fluids, exudate, blood clots and or bodily materials from the abdomen of a patient.

The function of a suction irrigator device is to continually evacuate fluids. The main problem associated is clogging, and slowing down the whole process. Typically, to overcome the clogging problems associated with suction irrigators and in order to maximizing fluid evacuation, multiple symmetrically located holes are incorporated along the distal end of the cannula. The inlets allow the suction device to continually operate. Even though this helps with small clots it does make the suction device less effective. In particular, when additional holes are utilized, they are placed along the proximal end of the device. These holes are relatively high in position to the body cavity and even though there are more of them they do not increase the suction force of the distal holes located in the body cavity. The additional suction force needs to take place where the clot is occurring.

One of the failures of having too many holes is loss of sucking action. It's not a question of having more suction holes but of applying the suction force in the correct location. The exposed holes suck more air instead of more fluids, and actually weaken the sucking force of the device at the distal end. By adding new holes near the proximal end, with no restricting device, the effective suction action of the device diminishes. When the distal holes become clogged instead of sucking harder and clearing the clot, the extra holes cause more air to be sucked at the proximal end and creates less sucking force at the distal end. The additional sucking force created by the additional holes is only effective when there are large amounts of fluids in the body cavity. Without the use of a restriction device the suction irrigator becomes less effective as the fluids decrease.

It should be noted that there continues to be a need in the field for a suction irrigator device that minimizes clogging and maximizes suction power at the distal end. Therefore, in a continuing effort to improve on surgical suction irrigation systems the present invention has been developed to overcome these and other similar deficiencies.

In order to overcome these problems, prior inventors have tried adding extra holes along the shaft to improve the suction force. Unfortunately, this does not solve the problem. It has been discovered that what is needed is a blocking means for the proximal openings that are just sucking air, and a means of redirecting the suction action to the openings or slits that are removing the clots or debris. It is the intention of this invention to incorporate a skirt device having a blocking mechanism along that shaft to filter out debris and dramatically increase the suction airflow.

In addition, the present invention has the ability to create more openings by simply bending the skirt section at the distal end. This serves several functions. First, it acts as a peanut device for moving debris within the body cavity. Secondly, the addition of openings at the distal end where the clots normally form allows better drainage and has a clot busting effect and permits the openings to be exposed at the lowest point in the cavity while allowing all the fluids to evacuate at the distal end.

When the sleeve device is lowered along the shaft it covers the openings that are not exposed to the fluids thus creating a stronger suction action where the dots are more likely to form.

In a continuing effort to improve on surgical endoscopic suction irrigation systems the present invention has been developed. The inventors of the present application have not found a similar device and believe this invention to be novel. There is a need in the field for a laparoscopic suction device that maintains its suction force throughout its use especially when clogging occurs.

In addition, the present invention is physically designed to breakup soft tissue into smaller pieces, so they can be easier to evacuate. Unlike any other suction device, the present invention uses a thin sharp feature at its distal opening for slicing the clots. In addition to this a skirt, mesh can overlap the distal end and act as a filter and peanut. When combined and connected with the unique universal attachment mechanism, the distal end shaft can spin 360 degrees without breaking its suction action. This permits the breakup of large clots into smaller manageable clots.

The main embodiment incorporates a canula tube connected fluidly within a mesh skirt. The external canula is not limited to but can be made of a clear material allowing itself to slide along the exterior of the elongated member and allow visibility to a screened skirt. There is a need in the field for a device that allows suction irrigation devices to perform properly while overcoming the common problems of clogging, weakened suction and longer surgical procedures.

Further features and embodiments will become apparent from the description and the accompanying drawings and the detailed description of the preferred embodiments which follow.

In an embodiment of the present invention, a laparoscopic anticlogging and clot busting device includes an elongated cannula having a proximal end and a distal end, at least one opening adjacent to the distal end, a sleeve slidably receiving the cannula, the sleeve being slidable between a first position where the sleeve covers the at least one opening, and a second position where the at least one opening is exposed In another embodiment of the present invention, a laparoscopic anticlogging and clot busting device includes an elongated cannula having a proximal end and a distal end, the proximal end being configured for attachment to a suction source, a distal opening at the distal end, a plurality of openings adjacent to the distal end and formed in a sidewall of the elongated cannula, and a sleeve slidably receiving the cannula. The sleeve is slidable between a first position where the sleeve covers the plurality of openings, and a second position where at least some of the plurality of openings are exposed so as to be in fluid communication with an environment outside of the sleeve.

In yet another embodiment of the present invention, a method for laparoscopic suctioning includes the steps of inserting a device having an elongated cannula having a proximal end and a distal end, at least one opening adjacent to the distal end, and a sleeve slidably receiving the cannula into a body of a patient, retracting the sleeve towards the proximal end of the cannula to expose the at least one opening to fluids within the body, providing suction to an interior passage of the cannula, and sliding the sleeve towards the distal end of the cannula to dislodge exudate from the at least one opening to unclog the at least one opening.

BRIEF DESCRIPTION OF DRAWINGS

The preferred embodiments of the invention will hereinafter be described in conjunction with the appended drawings provided to illustrate and not to limit the invention, in which.

Figure 1:
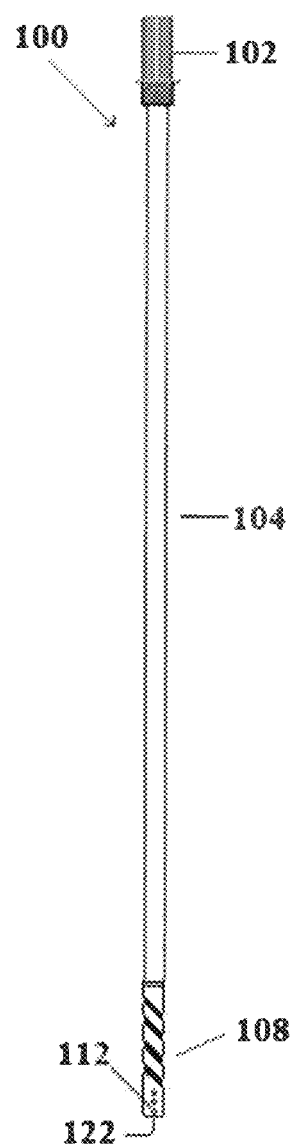
FIG. 1 is a perspective view of an exemplary embodiment of a Laparoscopic Anti-clogging Device according to an embodiment of the invention.

While the various features of this invention are hereinafter described and illustrated as being particularly adapted for providing rigidity to instrument devices the invention is not limited to the embodiments illustrated in the drawings but are merely used to illustrate the wide variety of uses of this invention. Therefore, the foregoing is considered as illustrative only of the principles of the invention. Since numerous modification and changes will readily occur by those skilled in the art, it is not desired to limit the invention to the exact construction and operation shown and described and accordingly, all suitable modifications and equivalents may be resorted to, falling within the scope of the invention.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1, unless otherwise stated. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

With respect to FIG. 1, a perspective view of a Laparoscopic Anti-clogging Device (100) according to an embodiment of the invention is shown. The device (100) includes an elongated body portion (104) in the form of a cannula having a proximal end and a distal end. The cannula (104) forms a hollow pathway for bodily liquids and exudate to exit an abdominal cavity (116) of a patient, as discussed hereinafter. The device (100) further includes handle or gripping portion (102) at the proximal end of the device (100), to which a suction device (not shown) may be attached, and includes a distal opening (122) in the distal end of the device (100). In the configuration illustrated in FIG. 1, no external sleeve is displayed. As further shown in FIG. 1, the device (100) includes a plurality of diagonal, spiral or helical openings or perforations (108) in the sidewall of the cannula (104) adjacent to the distal end of the cannula (104). These openings (108) are formed and oriented such that the distal end of the cannula (104) is made to be flexible (i.e., the distal end of the cannula (104) can flex and bend about these openings (108)). The openings (108) also provide a fluid pathway into the interior of the cannula (104) for sucking bodily liquids and exudate. As used herein, "exudate" means solid or semi-solid clots, tissue, bodily materials, etc. that may clog apertures or openings in a laparoscopic suction device. In an embodiment, the cannula (104) and perforated opening (108) can be made of metal, plastic, or any combination, such as a metal shaft and plastic flexible area. As also shown in FIG. 1, additionally, lateral openings or apertures (112) are provided adjacent to the distal end of the cannula (104) to assist in the suction action of opening (122), as described below.

Figure 2:
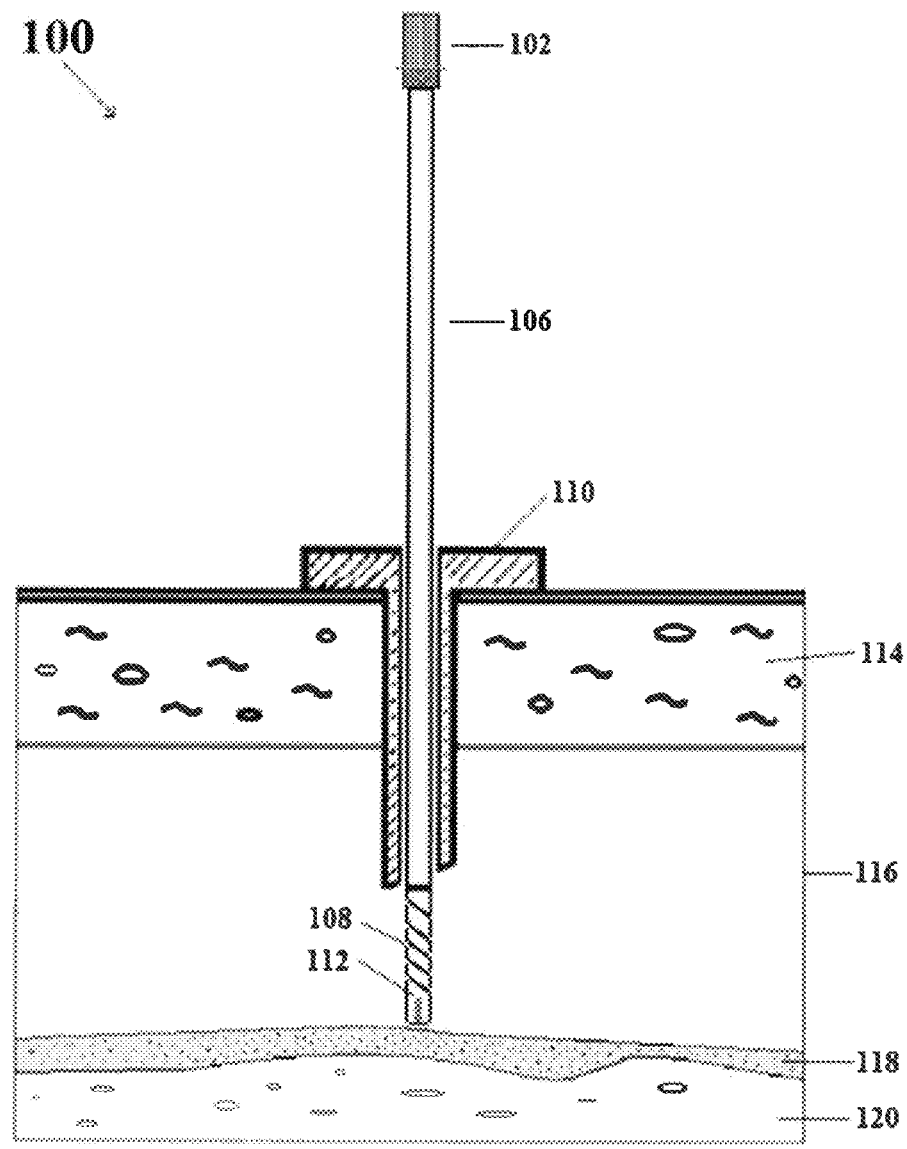
FIG. 2 is a partial, cross-sectional view of the Laparoscopic Anti-clogging Device inserted through a trocar in the abdomen.

FIG. 2 is a partial cross-sectional view illustrating the Laparoscopic Anti-clogging Device (100) inserted through a trocar (110) in an abdomen (116) of a patient. As shown therein, a trocar (110) may be inserted through the percutaneous skin (114) and into the abdominal cavity (116) of a patient, and the device (100) may then be passed through the trocar (110) until the distal end of the device (100) is positioned near fluids (118) (e.g., bodily fluids and/or exudate) adjacent to tissue or internal body organs (120) being operated upon. In this position. The Laparoscopic anti-clogging device (100) can be used to simply suck fluids (118) in its vertical position as some industry standard devices do.

Figure 3:
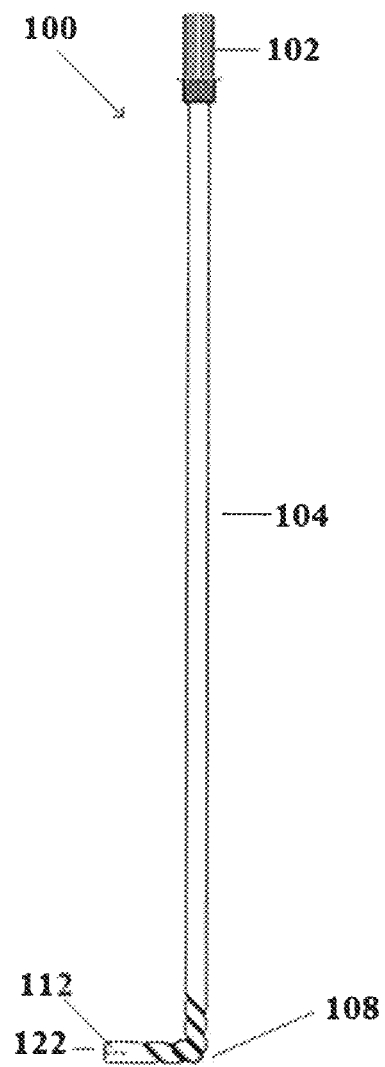
FIG. 3 is a side elevational view of the Laparoscopic Anti-clogging Device in an anticlogging position.

Turning now to FIG. 3, a side elevational view of the Laparoscopic Anti-clogging Device (100) is shown in an anticlogging position. As illustrated, the configuration of the perforated openings (108) (i.e., formed as a spiral or diagonal openings adjacent the distal end of the cannula) imparts flexibility to the distal end of the cannula allowing it to be bent or deformed. As shown, the distal end of the cannula (104) may be bend to an angle of 90 degrees or more with respect to a longitudinal axis defined by the cannula body. These openings (108) provide the ability for the distal end of the cannula (104) to become flexible and expand the diagonally perforated openings (108), which helps compensate for any obstruction, or blockage caused at the distal opening (122).

Figure 4:
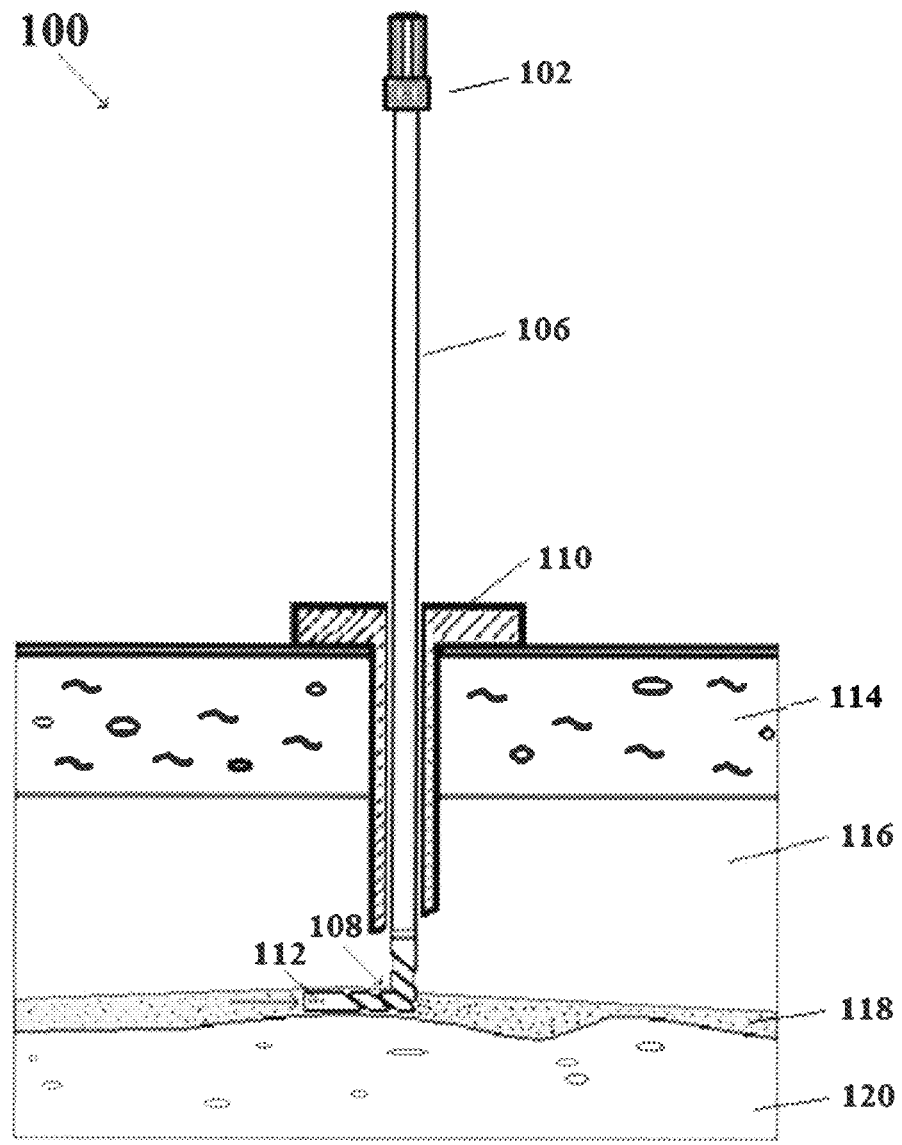
FIG. 4 is a side elevational view of the Laparoscopic Anti-clogging Device in a fully deployed anticlogging position inside an abdomen.

FIG. 4 illustrates the Laparoscopic Anti-clogging Device (100) in its fully deployed anticlogging position inside an abdomen (116), with the distal end in its bent or deformed position. At its distal end opening (122), fluids (118) are inhaled through the elongated canula device (104). Diagonally perforated openings (108) expand to increase the ingestion of fluids (118). A main advantage of this design is its ability to become flexible and overcome and clogging that may take place at the end opening (122).

Figure 5A:
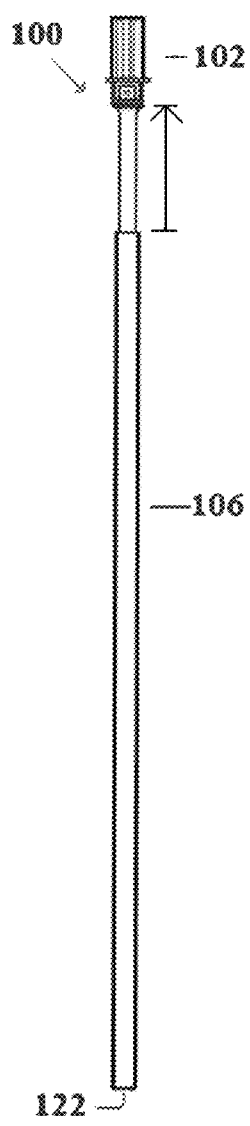
FIG. 5A is a plan view of the Laparoscopic Anti-clogging Device with an elongated sleeve in a covering position.
Figure 5B:
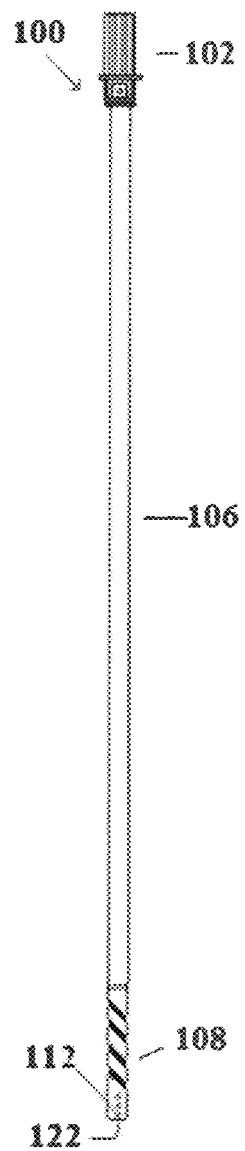
FIG. 5B is a plan view of the Laparoscopic Anti-clogging Device with an elongated sleeve exposing suction openings.
Figure 5C:
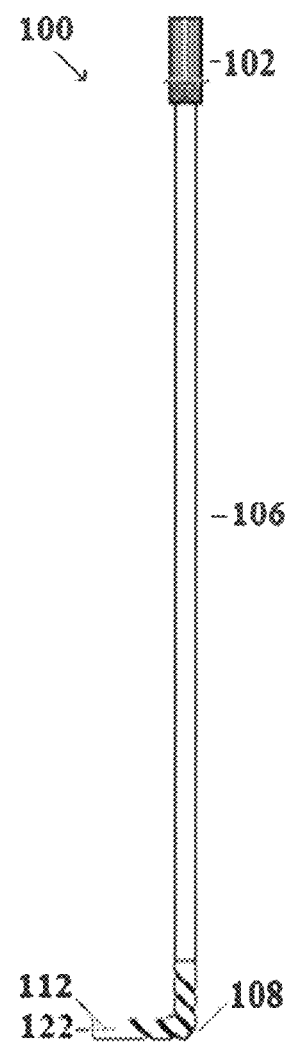
FIG. 5C is a plan view of the Laparoscopic Anti-clogging Device with an elongated sleeve exposing suction openings, in a preferred anti-clogging position/configuration.

With reference to FIGS. 5A-5C, in an embodiment, the Laparoscopic Anti-clogging Device (100) may further include a sheath or sleeve (106) which receives and surrounds the cannula (104). It is contemplated that the sleeve (106) may be metal, plastic or a cloth material, although other materials known in the art may also be utilized without departing from the broader aspects of the invention. The sleeve (106) is slidable along the cannula (104) to selectively cover/shield and expose the openings (108), (112) adjacent to the distal end of the cannula (104). For example, FIG. 5A illustrates the sleeve (106) in its deployed position, fully covering the openings (108), (112). The sleeve (106) is slidable towards the handle (102) to the retracted position shown in FIG. 5B, whereby the distal end of the cannula (104) extends from the sleeve (106) to expose the openings (108), (112). FIG. 5C likewise illustrates the sleeve (106) in a retracted position whereby the distal end of the cannula (104) extends from the sleeve (106) to expose the openings (108), (112), and where the distal end is bent to its ideal anti-clogging deployment. As indicated above, the perforated openings (108) expand when bent. When the sleeve (106) is moved to the retracted position, it exposes the perforated area (108) thus increasing the suction volume, which helps to overcome the deficiencies caused by fluid.

Figure 6:
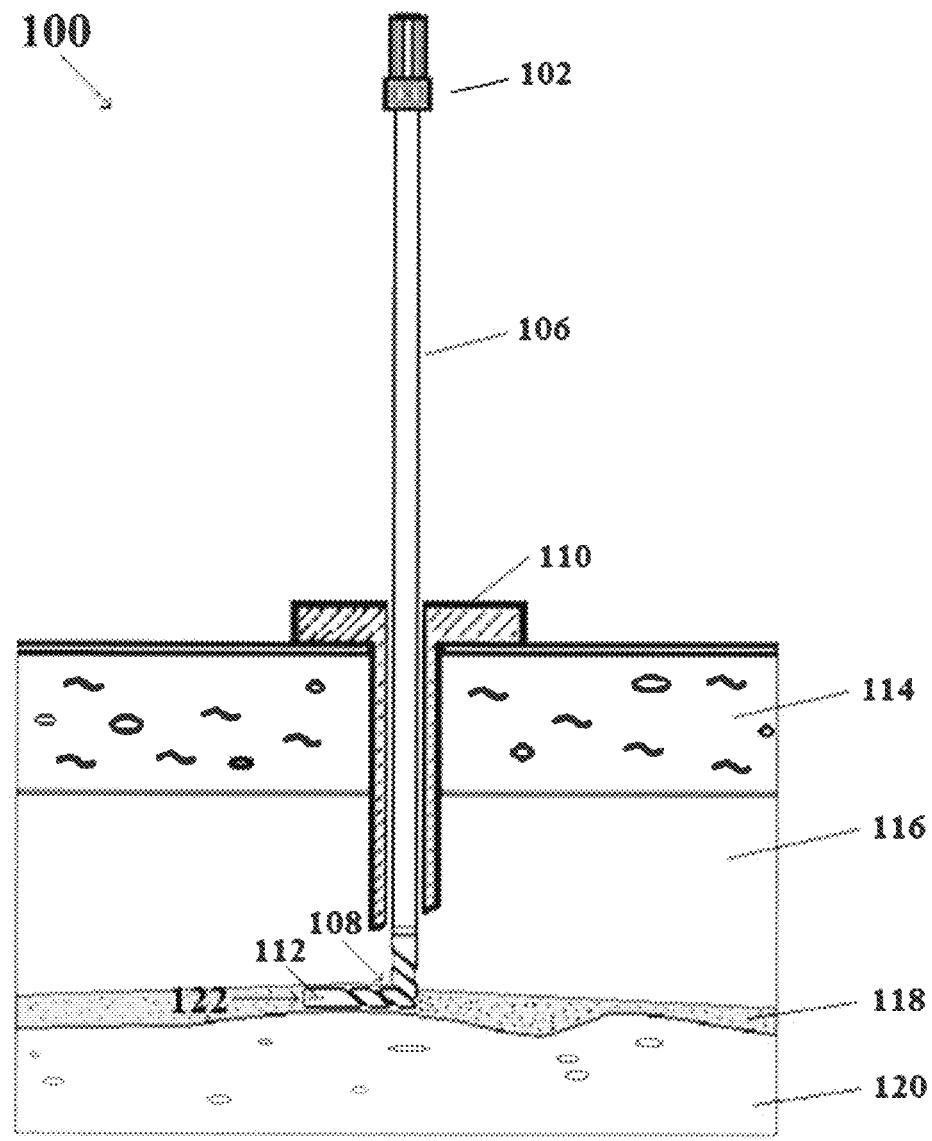
FIG. 6 is a plan view of the Laparoscopic Anti-clogging Device of FIGS. 5A-5C inserted through a trocar in the abdomen.

FIG. 6 is a partial cross-sectional view illustrating the Laparoscopic Anti-clogging Device (100) inserted through a trocar (110) in an abdomen (116) of a patient, with the sleeve (106) in its retracted position to expose the openings (108), (112), and with the distal end of the cannula (104) in its bent position. This position maximizes the suction capabilities of the device (100). In this position/orientation, the device (100) may suck fluids (118) either from the perforated openings (108) or and the distal end (122). It should be noted that one of the advantages of using the perforated openings is that a larger area is created for the inflow of fluids.

Figure 7A:
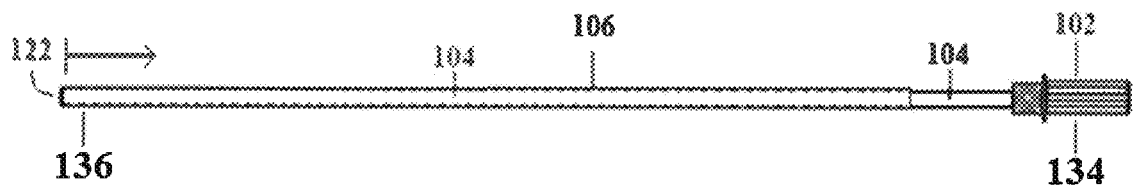
FIG. 7A is a plan view of a Laparoscopic Anti-clogging Device according to another embodiment of the invention, showing an expandable sheath in its pre-deployed position.
Figure 7B:
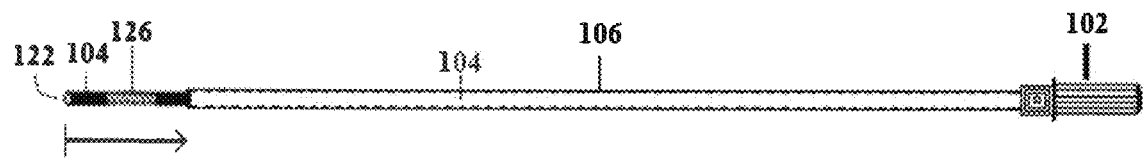
FIG. 7B is a plan view of the Laparoscopic Anti-clogging Device of FIG. 7A, showing the expandable sheath in its deployed position.

Turning now to FIG. 7A, a side elevational view of an alternative embodiment of the Laparoscopic Anti-clogging Device (100) is shown. As shown therein, the slidable sheath (106) is typically shorter in length then the elongated canula (104) and in its pre-deployed position covers a distal end (136) of the elongated canula (104). The distal end of the cannula (104) may be formed with an expandable sheath portion (126). When exposure to the expandable portion (126) is desired the elongated sleeve/sheath (106) is slid uniformly over and across the elongated canula (104) to the proximal end as is shown in FIG. 7B. FIG. 7B thus illustrates the elongated sheath (106) in its retracted position, but prior to having the expandable sheath (126) fully deployed.

Figure 7C:
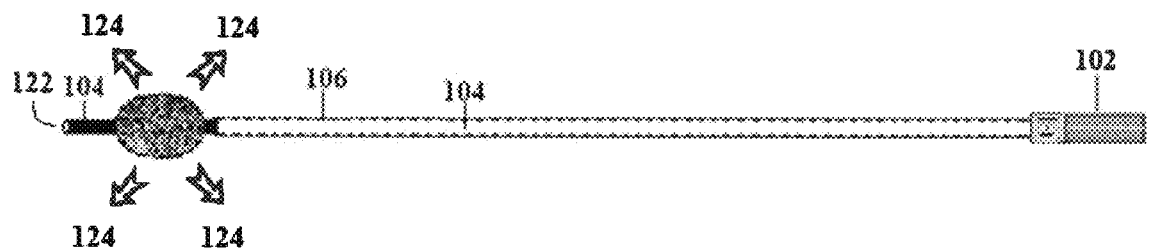
FIG. 7C is a plan view of the Laparoscopic Anti-clogging Device of FIG. 7A, showing the expanded sheath in its deployed position.

With respect to FIG. 7C, the Laparoscopic Anti-clogging Device (101) is shown having the expanded sheath (126) in its fully deployed position. The direction of suction is illustrated with arrows (124), and the expandable sheath (126) naturally expands in a shape/total surface area (e.g., a sphere or round object) providing a larger surface area permitting more fluids (118) to enter into the elongated canula area (104). The expandable sheath (126) is porous to fluids, and can be made of plastic, metal, mesh, screen, fabric, or other porous material, and can be composed or one or more layers. In an embodiment, the expandable sheath (126) is formed from a spring mesh such that when the sleeve (106) is retracted, the sheath (126) expands outwardly to encompass a larger volume, as illustrated in FIG. 7C. That is, in operation, as the sheath/sleeve (106) is moved to the retracted position, the expandable sheath (126) of the cannular (104) expands outwardly to provide a larger area of opening to the interior of the cannula for the passage of fluids into the cannula through the sheath (126).

Figure 8:
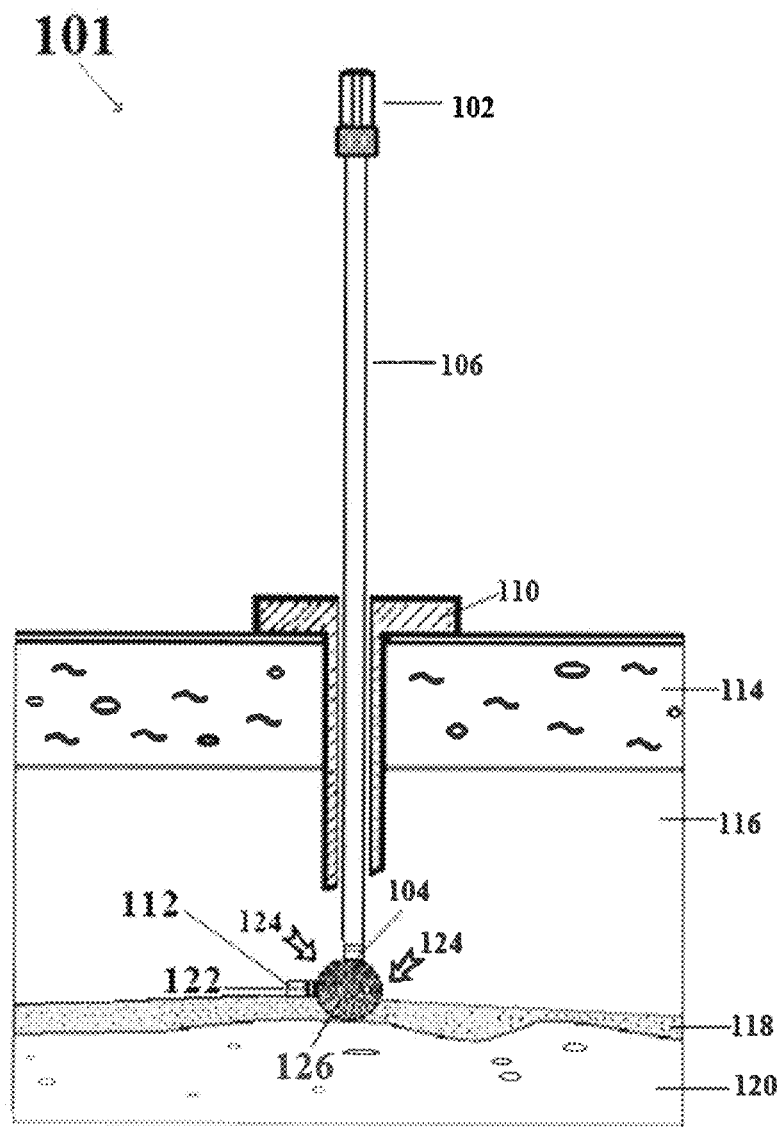
FIG. 8 is a partial, cross-sectional view perspective view of the Laparoscopic Anti-clogging Device of FIG. 7A deployed inside the abdomen.

Referring now to FIG. 8, an alternative embodiment of a Laparoscopic Anti-clogging Device (101) is shown fully deployed inside the abdomen (116) of a patient. Similar to the embodiment of FIGS. 7A-7C, the cannula (104) includes an expandable sheath or screen (126), which is depicted absorbing/suctioning fluids (118) from various positions. Fluids (118) can likewise be suctioned either and or through the side distal opening (112) and the distal opening (122) if either or several get clogged.

Figure 9A:
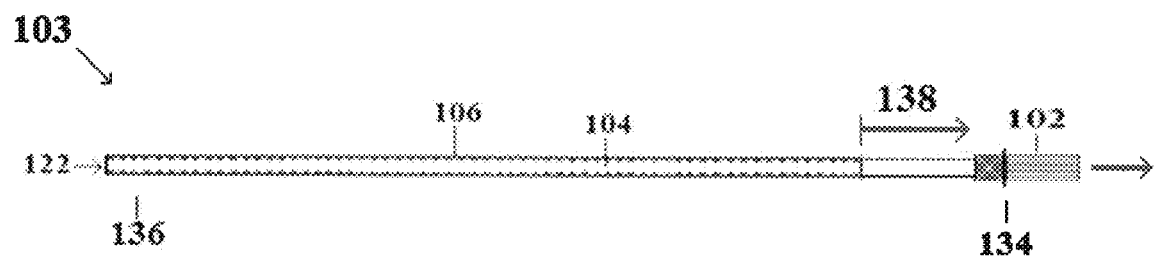
FIG. 9A is a plan view of a Laparoscopic Anti-clogging Device according to another embodiment of the invention, in its pre-deployed position.
Figure 9B:
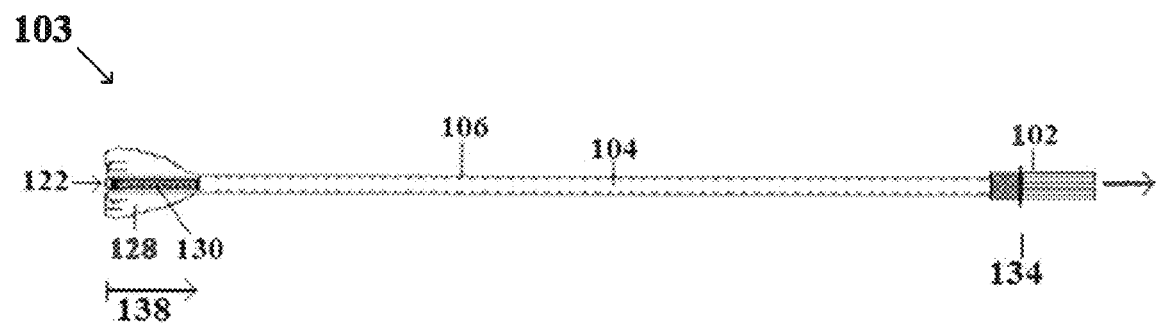
FIG. 9B is a perspective view of the Laparoscopic Anti-clogging Device of FIG. 9A in its deployed position.

FIGS. 9A and 9B illustrate another embodiment of a Laparoscopic Anti-clogging Device (103) according to an embodiment of the invention, which is generally similar in construction to the devices of the embodiments described above. The device (103) likewise has a slidable sleeve or (106) which is shown in its pre-deployed position in FIG. 9A. As shown in FIG. 9B, the cannula (104) may be formed with a substantially porous area (130) adjacent to the distal end. In an embodiment, for example, the porous area (130) may be formed from a porous material such as a screen, or may have a substantial portion (e.g. a majority) of the surface area comprised of apertures. As described above and as illustrated in FIG. 9B, the sleeve (106) is slidable towards the proximal end (134) to expose distance (138), thereby exposing porous area (130) of the cannula (104). In an embodiment, the porous area or layer (130) may be integrally formed in a wall of the cannula. Alternatively, the porous layer (130) may be an additional layer that surrounds the distal end of the cannula (104), including the openings (108), (112), where utilized. The porous layer (130) is separate from the openings (108), (112), and thereby creates a potential space between the tissues and the openings, allowing blood and liquids to be suctioned through the porous layer (130) and into the holes without allowing the tissues to block the pathway.

With particular reference to FIG. 9B, in an embodiment, the device (103) may include a skirt (128) that expands as it becomes exposed (via sliding of the sleeve (106) to the retracted position), providing a screening surface that permits fluids (118) to actively filter through. Like the expandable sheath, the skirt is porous to fluids, and can be made of plastic, metal, mesh, screen, fabric, or other porous material, and can be composed or one or more layers.

Figure 10:
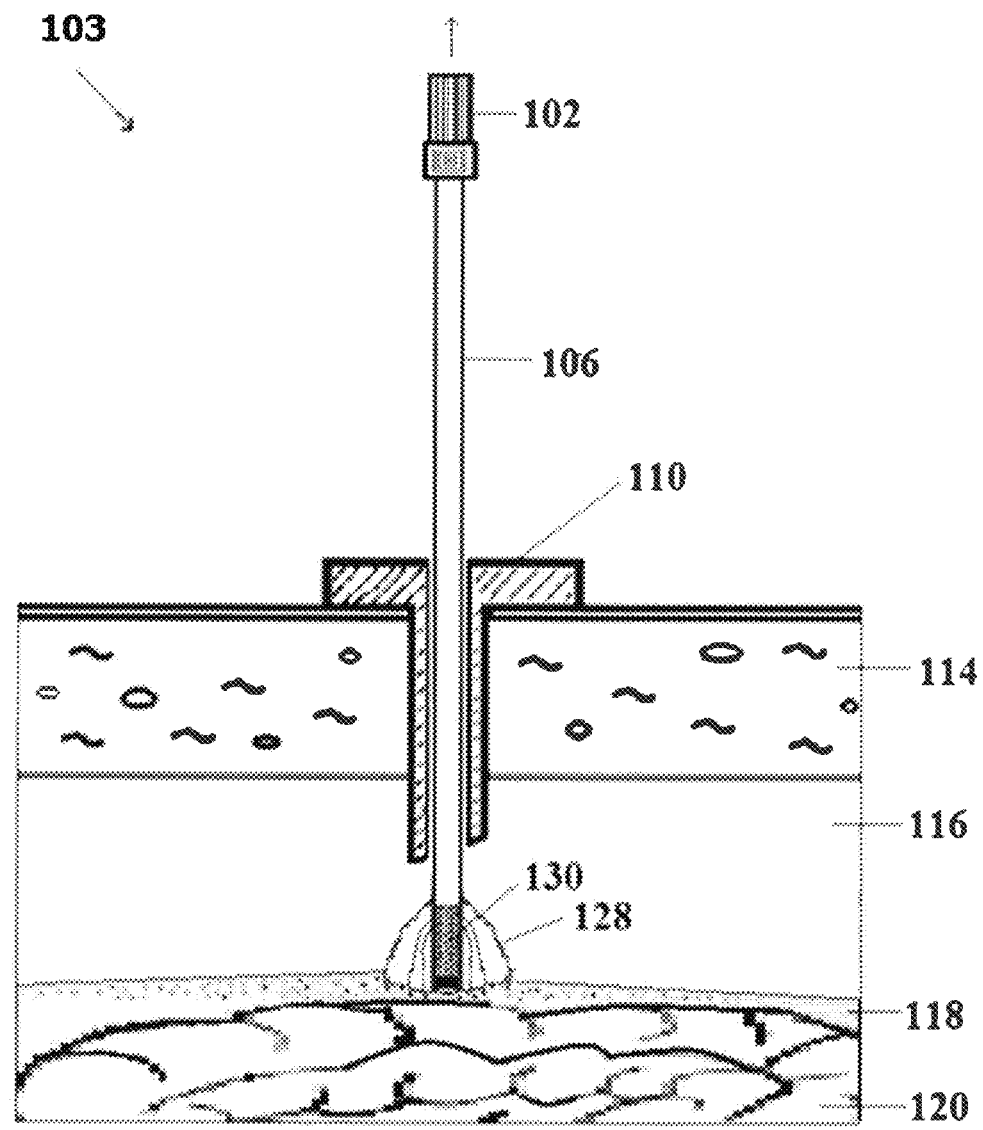
FIG. 10 is a partial, cross-sectional view of Laparoscopic Anti-clogging Device of claim 9A in a deployed position inside the abdomen.
Figure 11:
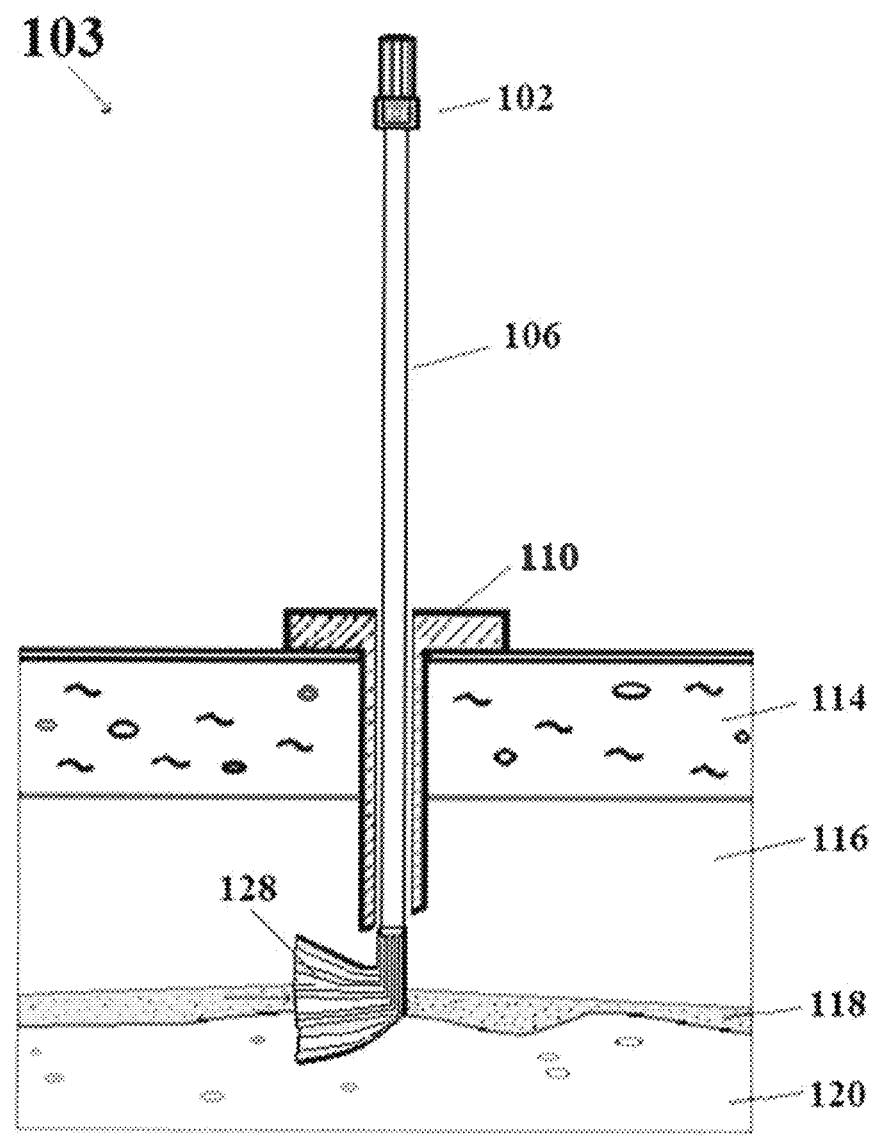
FIG. 11 is a perspective view of an embodiment of the Laparoscopic Anti-Clogging Device of FIG. 9A in its fully deployed position inside the abdomen using the skirt and cut out tubing.

Referring now to FIG. 10, the Laparoscopic Anti-clogging Device (103) of FIGS. 9A and 9B is shown fully deployed inside the abdomen (116) of a patient via insertion through a trocar (110), readably sucking fluids (118) and exudate. One advantage of this configuration is that the skirt (128) provides a soft, non-abrasive contact with the internal body organs (120). Skirt (128) additionally protects the elongated canula (104) from clogging by preventing tissue from entering the openings in the cannula (104). FIG. 11 illustrates the device (103) in its fully deployed, and flexibly-angled position inside the abdomen using the skirt and cut out tubing.

Figure 12:
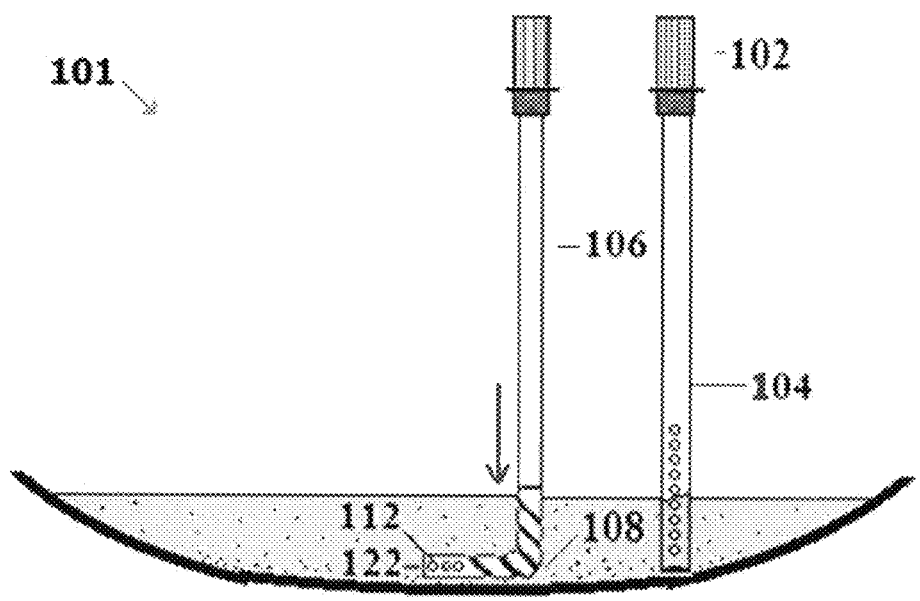
FIG. 12 is a perspective view of an embodiment of the Laparoscopic Anti-Clogging Device of FIG. 9A bent in an L shape demonstrating how it sucks out liquids.

Turning finally to FIG. 12, a simplified-cross sectional view of the device (101) is shown in bent position exposing the diagonally perforated slits/openings (108), which permits larger amounts of fluid/tissue volume to be evacuated. This is in contrast to a non-flexible cannula with multiple openings arrayed longitudinally along the cannula. As shown there, with the device (101), a larger percentage of the openings may be positioned below a fluid level within a body cavity due to the flexible distal end, as compared to a simple evacuation tube having multiple perforations arranged vertically along the tube.

Importantly, in addition to allowing for the selective exposure of the suction openings in the lateral sidewall of the cannula, the sleeve is also utilized to remove exudate which may clog the openings. In particular, if the lateral openings (e.g., openings (108), (112) or porous material/screen becomes clogged during use, the sleeve (106) may be moved toward the distal end of the cannula (104), contacting the exudate and urging or pushing it out of the openings. In this manner, the sleeve (106) can be utilized to unclog the openings during use so that the surgical procedure does not have to be halted or any instrumentation removed from the body of the patient.

A laparoscopic anticlogging and clot busting device according to an embodiment of the invention includes a proximal handle, an elongated cannula having openings therein, the distal end of the cannula, further including an elongated sleeve/sheath that extends to the distal end for removing exudate which may clog the distal end. The device has a handle used to hold the device in place when the sleeve is extended downwardly to the distal end. The device having openings diagonally perforated to expand and increase volume of fluids and exudate being pulled therein, the distal end made flexible to bend and open overcoming any clogging of the distal opening.

The device may also further include a skirt which consists of a porous layer that is separated from the openings, and thereby creates a space between the tissues and the openings, allowing blood and liquids to be suctioned through the layer and into the openings without allowing the tissues to block the path. Wherein the skirt is exposed when the sleeve is retracted proximately.

The distal end contains a plurality of diagonally perforated openings, the openings being symmetrically located at the distal end allowing better suction of fluids, blood and particles of exudate. An expanded sheath which allows fluids to pass therethrough and opening to allow a greater amount of material to be evacuated in less time.

The device having a shaft and perforated opening that can be made of metal, plastic, or any combination thereof.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

What is claimed is:

1. A laparoscopic anticlogging and clot busting device, comprising:
    an elongated cannula having a proximal end and a distal end;
    at least one opening adjacent to the distal end, the distal end of the cannula being flexible such that an area of the at least one opening is increased when the distal end of the cannula is bent; and
    a sleeve slidably receiving the cannula, the sleeve being slidable between a first position where the sleeve covers the at least one opening, and a second position where the at least one opening is exposed,
    wherein an increase in the area of the at least one opening increases a volume of fluids that is permitted to pass through the at least one opening and into an interior of the cannula, and
    wherein the distal portion of the cannula is bendable to an angle of approximately 90 degrees with respect to a longitudinal axis of the cannula.

2. The device of claim 1, further comprising:
    a handle at the proximal end;
    wherein the handle is used to hold the device in place when the sleeve is extended downwardly to the distal end.

3. The device of claim 1, wherein:
    the sleeve is slidably movable from the second position to the first position to remove exudate from the at least one opening to unclog the at least one opening.

4. The device of claim 1, wherein:
    the at least one opening is a plurality of openings in a diagonal orientation on the distal end of the cannula.

5. The device of claim 1, wherein:
    the at least one opening is arranged in a spiral or helical configuration.

6. The device of claim 1, wherein:
    the at least one opening is a plurality of slits adjacent to the distal end of the cannula.

7. The device of claim 1, further comprising:
    a skirt defining a porous layer that is separated from the at least one opening, the skirt functioning as a filter to allow blood and liquids to be suctioned through the skirt and into the at least one opening without allowing tissue which can clog the at least one opening to pass through the skirt.

8. The device of claim 7, wherein:
    the skirt is exposed when the sleeve is moved to the second position.

9. The device of claim 1, further comprising:
    an expandable sheath adjacent to the distal end of the cannula, the expandable sheath being expandable in surface area providing a larger area of opening to an interior of the cannula;
    wherein in an expanded state, the expandable sheath has a spherical shape.

10. The device of claim 9, wherein:
    the expandable sheath is porous to fluids.

11. A laparoscopic anticlogging and clot busting device, comprising:
    an elongated cannula having a proximal end and a distal end, the proximal end being configured for attachment to a suction source;
    a distal opening at the distal end;
    a plurality of openings adjacent to the distal end and formed in a sidewall of the elongated cannula, the distal end of the cannula being flexible such that an area of the at least one of the plurality of openings is increased when the distal end of the cannula is bent;
    a sleeve slidably receiving the cannula, the sleeve being slidable between a first position where the sleeve covers the plurality of openings, and a second position where at least some of the plurality of openings are exposed so as to be in fluid communication with an environment outside of the sleeve; and
    a skirt received about the distal end of the cannula and over the plurality of openings, the skirt forming a porous layer over the plurality of openings, the skirt functioning as a filter to allow blood and liquids to be suctioned through the skirt and into the plurality of openings while excluding tissue fragments or debris from clogging the plurality of openings,
        wherein an increase in the area of the at least one opening increases a volume of fluids that is permitted to pass through the plurality of openings and into an interior of the cannula.

12. The device of claim 11, further comprising:
    the sleeve is slidably movable from the second position to the first position to remove exudate from the plurality of openings to unclog the plurality of openings.

13. The device of claim 12, wherein:
    the plurality of openings are in a spiral or helical configuration.

14. The device of claim 12, wherein:
    the plurality of openings are a plurality of slits adjacent to the distal end of the cannula.

15. The device of claim 11, wherein the skirt includes of one or more layers of mesh, screen or fabric.

16. A method for laparoscopic suctioning, comprising the steps of:
    inserting a device into a body of a patient, the device having an elongated cannula having a proximal end and a distal end, at least one opening adjacent to the distal end, and a sleeve slidably receiving the cannula;
    retracting the sleeve towards the proximal end of the cannula to expose the at least one opening to fluids within the body;
    providing suction to an interior passage of the cannula;

sliding the sleeve towards the distal end of the cannula to dislodge exudate from the at least one opening to unclog the at least one opening; and enlarging an area of the at least one opening by bending a distal end portion of the cannula to an angle of approximately 90 degrees with respect to a longitudinal axis of the cannula.

\* \* \* \* \*